United States Patent [19]

Nishi

[11] Patent Number: 5,171,320
[45] Date of Patent: Dec. 15, 1992

[54] INTRAOCULAR LENS HAVING ANNULAR GROOVE FORMED IN ITS PERIPHERAL PORTION

[75] Inventor: Okihiro Nishi, Katano, Japan

[73] Assignee: Menicon Co., Ltd., Japan

[21] Appl. No.: 647,364

[22] Filed: Jan. 29, 1991

[30] Foreign Application Priority Data

Nov. 30, 1990 [JP] Japan .............................. 2-130340[U]

[51] Int. Cl.⁵ ............................................... A61F 2/16
[52] U.S. Cl. ......................................................... 623/6
[58] Field of Search ............................................ 623/6

[56] References Cited

U.S. PATENT DOCUMENTS

| | | | |
|---|---|---|---|
| 4,172,297 | 10/1979 | Schlegel | 623/6 |
| 4,206,518 | 6/1980 | Vardon et al. | 623/6 |
| 4,285,072 | 8/1981 | Morcher et al. | 623/6 |
| 4,342,123 | 8/1982 | Gimbel | 623/6 |
| 4,485,498 | 12/1984 | Gimbel | 623/6 |
| 4,605,409 | 8/1986 | Kelman | 623/6 |
| 4,676,792 | 6/1987 | Praeger | 623/6 |

FOREIGN PATENT DOCUMENTS 63-200755 8/1988 Japan .
64-32859 2/1989 Japan .

Primary Examiner—Ronald Frinks
Attorney, Agent, or Firm—Parkhurst, Wendel & Rossi

[57] ABSTRACT

An intraocular lens system adapted to be implanted within a generally circular opening in an anterior wall of the capsular bag which normally contains the crystalline lens of an eye. The intraocular lens system includes a lens body having an annular groove which is formed in a peripheral portion thereof in a plane substantially perpendicular to an optical axis of the lens body. The lens body includes an optically effective portion located radially inside the annular groove, and an anterior lens portion and a posterior lens portion located on respective anterior and posterior sides of the annular groove. The intraocular lens system is secured in position within the circular opening such that an annular flap portion of the capsular bag which surrounds the circular opening is accommodated within the annular grove in the lens body.

13 Claims, 6 Drawing Sheets

INTRAOCULAR LENS HAVING ANNULAR GROOVE FORMED IN ITS PERIPHERAL PORTION

BACKGROUND OF THE INVENTION

1. Field of the Invention

The present invention relates in general to an artificial intraocular lens intended for implanting within the human eye, which lens is mounted on a capsular bag normally containing the natural crystalline lens of the eye, after removal of the crystalline lens from the capsular bag. More particularly, this invention is concerned with an intraocular lens that is secured in an opening in the anterior wall of the capsular bag for that facilitated removal of the nucleus of the crystalline lens from the bag.

2. Discussion of the Prior Art

According to one of known methods for cataract surgery, an opening is provided in a capsule or capsular bag in which the crystalline lens of the normal eye is contained by surgically removing a portion of the anterior wall of the capsular bag. The opening is provided so that the nucleus of the crystalline lens can be extracted through the opening from within the capsular bag. Subsequently, an artificial intraocular lens serving as a substitute for the crystalline lens is inserted through the opening into the capsular bag.

The above-described method is advantageous in that the intraocular lens within the capsular bag is prevented by the remaining portion of the anterior wall of the bag from moving forward, that is, moving toward the cornea. Where the partial removal of the capsular bag is effected according to a so-called CCC (continuous circular capsulorhexis) method, the opening provided in the bag has a circular shape having a high degree of peripheral continuity. In this case, an annular flap portion of the capsular bag which surrounds or defines the opening is unlikely to tear even with stress concentration taking place thereon, whereby the slipping-off or displacement of the intraocular lens due to the tearing of the annular flap portion of the bag is effectively avoided.

As a long period of time elapses after a portion of the capsular bag is surgically removed, however, the growth of ocular tissue or proliferation of epithelial cells develops at the annular flap portion of the bag surrounding the opening, whereby the opening is gradually closed by collagenous fibers produced during the proliferation, or due to adhesion of the annular flap portion of the bag to the intraocular lens. Consequently, the front surface of the intraocular lens inserted within the capsular bag is progressively covered by the collagenous fibers and/or the anterior wall of the bag which has been made opaque, causing problems such as distortion of an image focused by the lens and poor transparency of the intraocular lens eye. Further, since the intraocular lens is not secured in position within the capsular bag, the lens suffers from displacement or dislocation due to shrinking of the capsular bag.

In view of the above, there is proposed an intraocular lens system as disclosed in U.S. Pat. No. 4,342,123, which has a lens body, and at least one inter-acting pair of clips which are secured to the lens body so that a flap portion of the anterior wall of the capsular bag which surrounds the opening is gripped by and between each pair of clips. Thus, the lens body of the intraocular lens system is fixedly held in position within the opening in the capsular bag. That is, the lens system can be secured in position in the opening such that the anterior portion of the lens is located outside the capsular bag, to thereby prevent the front surface of lens from being covered by the anterior wall of the capsular bag.

In the disclosed intraocular lens system, however, the annular flap portion of the anterior wall of the capsular bag surrounding the opening remains uncovered, permitting the proliferation of the cells a the flap portion of the bag. Due to this proliferation, the annular flap portion of the capsular bag expands or grows along the surface of the lens, and eventually covers an optical lens portion of the lens body. Consequently, the anterior or posterior surface of the lens becomes opaque, and the opening provided in the capsular bag is inevitably closed by the thus expanded flap portion of the bag, even though the anterior portion of the lens is located outside the bag as described above.

In the lens system disclosed in the U.S. patent identified above, there is a possibility that the iris of the eye as well as the flap portion of the capsular bag is gripped by and between the pair of clips, since the clips are made relatively large enough to provide a sufficient gripping force so as to hold the lens system in position. Further, since the intraocular lens system is held in position with the pair of clips engaging the flap portion, there has been the risk of dislocation or dropout of the intraocular lens when the gripping force of the clips is reduced with a lapse of time, or when a relatively large shock is applied to the lens, for example.

SUMMARY OF THE INVENTION

The present invention was developed in the light of the problems encountered in the prior art. It is accordingly an object of the invention to provide an intraocular lens system which can be securely held in position at the center of the eye, without subsequently closing an opening provided in the anterior wall of the capsular bag, and without causing subsequent displacement of the lens within the eye.

The above object may be attained according to the principle of the present invention, which provides an intraocular lens system adapted to be implanted within a generally circular opening in an anterior wall of the capsular bag which normally contains the crystalline lens of an eye, comprising a lens body having an annular groove which is formed in a peripheral portion thereof in a plane substantially perpendicular to an optical axis of the lens body, the lens body including an optical portion located radially inside the annular groove, and an anterior lens portion and a posterior lens portion located on respective anterior and posterior sides of the annular groove, the intraocular lens system being secured in position within the circular opening such that an annular flap portion of the capsular bag which surrounds or defines the circular opening is accommodated within the annular groove in the lens body.

In the intraocular lens system constructed as described above according to the present invention, the annular flap portion of the capsular bag defining or surrounding the circular opening is circumferentially entirely accommodated in the annular groove formed in the peripheral portion of the lens body. Accordingly, the periphery of the flap portion otherwise adjacent to the periphery of the intraocular lens body is placed within the groove, thereby preventing the proliferation of the cells which occurs at the peripheral part of the flap portion. Thus, the present lens system is firmly secured in position within the opening, that is, at the center of the anterior wall of the capsular bag, without suffering from the dislocation of the lens due to the shrinking of the capsular bag. Further, the present lens system is stably held in place for a prolonged period of time.

With the present lens system secured in position, the proliferation of the cells of the annular flap portion of the capsular bag takes place only within the annular groove having a suitable depth. Thus, the groove is adapted to accommodate the collagenous fibers as a result of the proliferation, so that the growth of the variant anterior wall of the capsular bag is limited within the groove in the lens body. Accordingly, the anterior wall of the capsular bag is prevented from covering the anterior or posterior surface of the intraocular lens, thus avoiding closure of the opening by the collagenous fibres. Thus, the present lens system can exhibit stable and excellent optical capability for a prolonged period of time.

In one preferred form of the present invention, at least a part of the posterior lens portion is located radially outwardly of the anterior lens portion as viewed in a direction parallel to the optical axis of the lens body. In this case, the radial distance from the bottom of the groove to the periphery of the above-indicated part of the posterior lens portion is made larger than the radial distance from the bottom of the groove to the periphery of the corresponding part of the anterior lens portion. Therefore, the present intraocular lens system is favorably prevented from moving forward or slipping off toward the cornea due to external shocks, for example, assuring significantly improved safety.

In another preferred form of the invention, the anterior and posterior lens portions have substantially the same dimensions and the same configuration as viewed in a direction of the optical axis of the lens body. In this arrangement, the annular groove may have a longer diameter than that of the groove which is formed in the lens body whose anterior lens portion has a smaller dimension than the posterior lens portion. In other words, substantially the entire area of the lens body except the extreme peripheral portion which defines the groove may be utilized as the optical lens portion. Thus, the present intraocular lens system has a relatively large optical lens portion, assuring significantly improved optical capability, even if the lens body is somewhat dislocated from the nominal position upon mounting of the lens system on the capsular bag.

According to one feature of the above form of the invention, the intraocular lens system further includes support means secured to the posterior portion of the lens body, for holding the lens body against the posterior surface of the anterior wall of the capsular bag. In this arrangement, the intraocular lens is secured in position with respect to the anterior wall of the capsular bag, with the support means preventing the lens from moving forward or slipping off toward the cornea due to external shocks, for example. Since the support means included in the present lens system is merely required to function for preventing slipping-off of the lens body, the support means may be relatively small-sized, as compared with the conventional counterpart having a pair of relative large clips adapted to hold the anterior wall of the capsular bag therebetween to secure the lens without an annular groove. Further, the support means can be placed within the capsular bag, without interfering with the iris of the eye.

BRIEF DESCRIPTION OF THE DRAWINGS

The above and optional objects, features and advantages of the invention will be better understood by reading the following description of some presently preferred embodiments of the invention, when considered in conjunction with the accompanying drawings, in which:

FIG. 1a is a plan view of one embodiment of an intraocular lens system of the present invention;

FIG. 1b is a cross sectional view of the lens system of FIG. 1a, taken along line B—B of FIG. 1a;

DETAILED DESCRIPTION OF THE PREFERRED EMBODIMENTS

The intraocular lens constructed according to the present invention is formed of a known material as used for ordinary intraocular lenses. For example, the lens is formed of highly transparent synthetic resin, such as polymethyl methacrylate, polyhydroxyethyl methacrylate and silicone rubber, or formed of a glass material.

The intraocular lens of the present invention has a groove formed in its peripheral portion, which is located radially outside the optically effective portion of the lens. This groove is formed in annular configuration in a plane substantially perpendicular to an optical axis of the lens. The capsular bag of the eye has a complementary generally circular opening formed through its anterior surface, within which the intraocular lens is secured in position such that an annular flap portion of the capsular bag surrounding the opening is held in engagement with the annular groove in the lens over the entire circumference thereof.

Figures 1A, 1B:
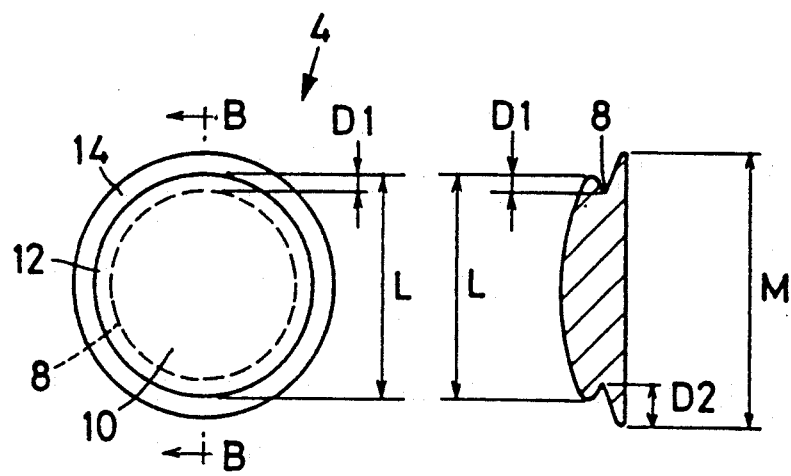

Referring first to FIGS. 1a and 1b, reference numeral 4 denotes an intraocular lens which is formed according to one embodiment of the present invention. The intraocular lens 4 has an annular groove 8 formed in its radially peripheral portion such that an optically effective portion 10 of the lens is located radially inside the groove 8. The lens 4 consists of an anterior lens portion 12 and a posterior lens portion 14, which are respectively located on the front and rear sides of the groove 8 as viewed in a direction parallel to the optical axis of the lens 4. The anterior lens portion 12 has a circular shape having a diameter "L" while the posterior lens portion 14 has a circular shape having a diameter "M" which is larger than "L", as shown in FIGS. 1a and 1b.

In the intraocular lens 4 as described above, it is desirable that the diameter of the optically effective portion 10 is within a range of about 3 mm to 8 mm, and that the depth of the groove 8 is within a range of 0.1 mm to 2 mm. If the depth of the groove 8 is smaller than 0.1 mm, the annular flap portion of the capsular bag is likely to be disengaged from the groove 8 after the lens 4 is placed within the opening provided in the anterior wall of the capsular bag. The groove 8, whose depth is larger than 2 mm, does not optically effect the lens 4 according to the invention, but such a depth makes it difficult to insert or accommodate the annular flap portion of the capsular bag into the groove 8. Further, the intraocular lens 4 with the groove 8 having a depth larger than 2 mm tends to be large-sized because of the relatively large depth of the groove 8, making it difficult to insert the lens 4 through an opening which is surgically provided in the cornea of the eye. As will be understood from FIGS. 1a and 1b, the depth of the groove 8 formed in the intraocular lens 4 is defined as a smaller one of a radial dimension D1 from the periphery of the anterior lens portion 12 to the bottom of the groove 8, and a radial dimension D2 from the periphery of the posterior lens portion 14 to the bottom of the groove 8.

Since the intraocular lens 4 as shown in FIGS. 1a, 1b is constructed such that the diameter L of the anterior lens portion 12 is smaller than the diameter M of the posterior lens portion 14, the rim of the posterior lens portion 14 is located radially outwardly of the anterior lens portion 12 over the entire circumference of the lens portions 12, 14 as viewed in the direction of the optical axis of the lens 4. That is, the radial dimension D2 on the side of the posterior lens portion 14 is made larger than the radial dimension D1 on the side of the anterior lens portion 12 over the entire circumference thereof. In this arrangement, the intraocular lens 4 is excellently prevented from moving away from the capsular bag toward the cornea owing to an externally applied shock, or a pressure applied from the vitreous humour, assuring significantly improved safety and stabilization of the lens 4 within the eye.

It is to be understood that the radial dimension D2 is not necessarily larger than the radial dimension D1 over the entire circumference of the lens 4. Namely, the effect as provided in the embodiment of FIG. 1 can be similarly obtained even where only a part or parts of the posterior lens portion 14 has/have the radial dimension D2 larger than the radial dimension D1 on the side of the anterior lens portion 12. Although it is preferred that the anterior and posterior lens portions 12, 14 both assume a circular shape in view of ease of manufacturing the intraocular lens 4, the shapes of these portions 12, 14 are not particularly limited, as long as the groove 8 is formed in annular or closed-loop configuration. For instance, the effect of the invention as described above may be similarly obtained by intraocular lenses 13, 15 and 17, as respectively shown in FIGS. 2, 3 and 4, which are constructed according to other embodiments of the invention. In these figures, the same numerals as used in the embodiment of FIG. 1 will be used for identifying functionally corresponding elements, and no detailed description of these elements will be provided.

Figure 2:
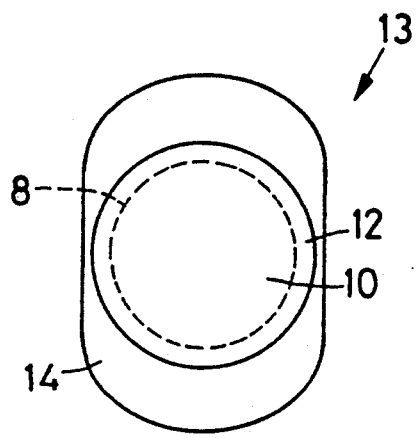
FIGS. 2, 3 and 4 are plan views showing other embodiments of the intraocular lens system of the present invention.

In the intraocular lens 13 as shown in FIG. 2, the anterior lens portion 12 has a circular shape, while the posterior lens portion 14 has a generally rectangular shape with its opposite shorter sides having semicircular or arcuate profiles. The depth of the groove 8 is equal to the radial dimension D1, which is constant over the entire circumference of the lens 13. Accordingly, the intraocular lens 13 is favorably prevented from slipping off or moving away from the capsular bag toward the cornea. While the radial dimension D2 on the side of the posterior lens portion 14 is not constant over the entire circumference of the lens 13, this does not cause any problem as long as the radial dimension D1 on the side of the anterior lens portion 12 is determined to be smaller than 2 mm.

Figures 3, 4:
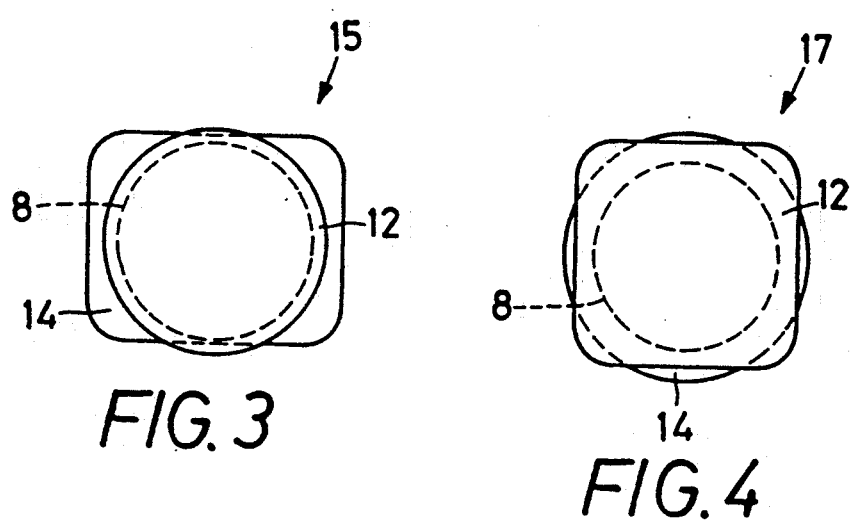

In the intraocular lens 15 as shown in FIG. 3, the anterior lens portion 12 has a circular shape while the posterior lens portion 14 has a generally rectangular shape, as viewed in the direction of the optical axis of the lens 15. The intraocular lens 15 is dimensioned such that the width of the posterior lens portion 14 is smaller than the diameter of the anterior lens portion 12, and such that the length of the posterior lens portion 14 is larger than the diameter of the anterior lens portion 12. Therefore, the radial dimension D1 is larger than the radial dimension D2 at a middle part of each of the longitudinally extending opposite edges of the posterior lens portion 14, while the radial dimension D1 is smaller than the radial dimension D2 at the other parts of the posterior lens portion 14. Also in this arrangement, the intraocular lens 15 is prevented from being dislocation due to any forward and backward movements along the optical axis of the lens 15.

In the intraocular lens 17 as shown in FIG. 4, the anterior lens portion 12 assumes a generally square shape, and the posterior lens portion 14 assumes a circular shape, as viewed in the direction of the optical axis of the lens 17. The radial dimension D1 on the side of the anterior lens portion 12 is larger than the radial dimension D2 on the side of the posterior lens portion 14 at each of four corner sections of the square anterior lens portion 12, while the radial dimension D2 is larger than the radial dimension D1 at the other parts of the lens portion 12. Thus, the intraocular lens 17 is also prevented from being dislocated in both the forward and backward directions along the optical axis of the lens 17.

It will be understood from the above description that the intraocular lens having the annular groove in its periphery is firmly secured in position within the opening in the anterior wall of the capsular bag, such that the annular flap portion of the bag surrounding or defining the opening is held in engagement with the annular groove. This arrangement also prevents the closure of the opening due to proliferation of the cells at the annular flap portion of the capsular bag. When the radial dimension on the side of the posterior lens portion is made larger than that on the side of the anterior lens portion, the present intraocular lens is favorably prevented from being removed from the capsular bag toward the cornea.

In order to improve prevention of the intraocular lens from slipping off or moving away from the capsular bag, it is possible to provide suitable support means for attaching the lens to the anterior wall of the capsular bag. This support means may take the form of a U- shaped loop, C-shaped loop or J-shaped loop, which is widely used for attachment of the lens, and which is usually formed of a synthetic resin, such as polyamide, polyimide, polypropylene, polyvinylidene fluoride, polymethyl methacrylate, polyhydroxyethyl methacrylate and silicone rubber. Further, the position of attachment of the support means with respect to the intraocular lens is not particularly limited.

Figures 5A, 5B:
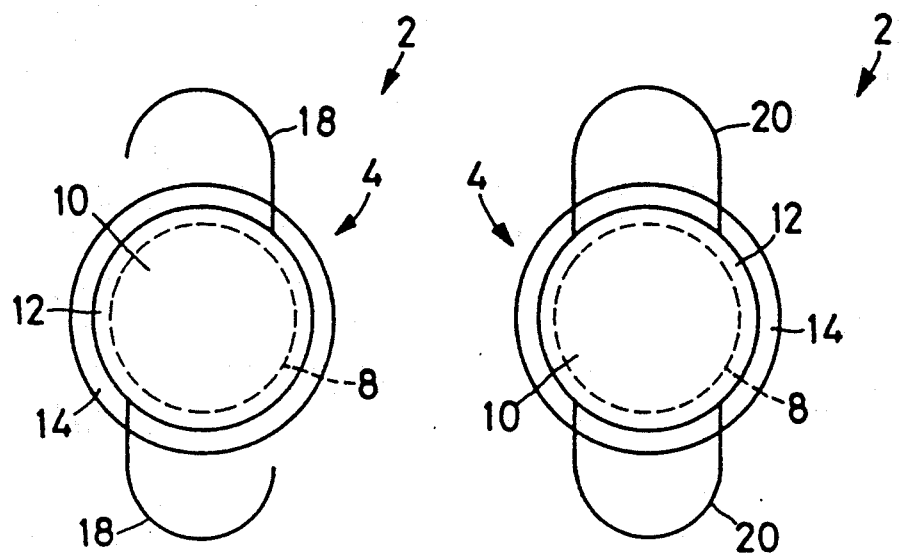
FIGS. 5a and 5b are plan views showing intraocular lens systems similar to that of FIG. 1, each lens system having a pair of loops secured to an anterior lens portion of a lens body.
Figures 6A, 6B:
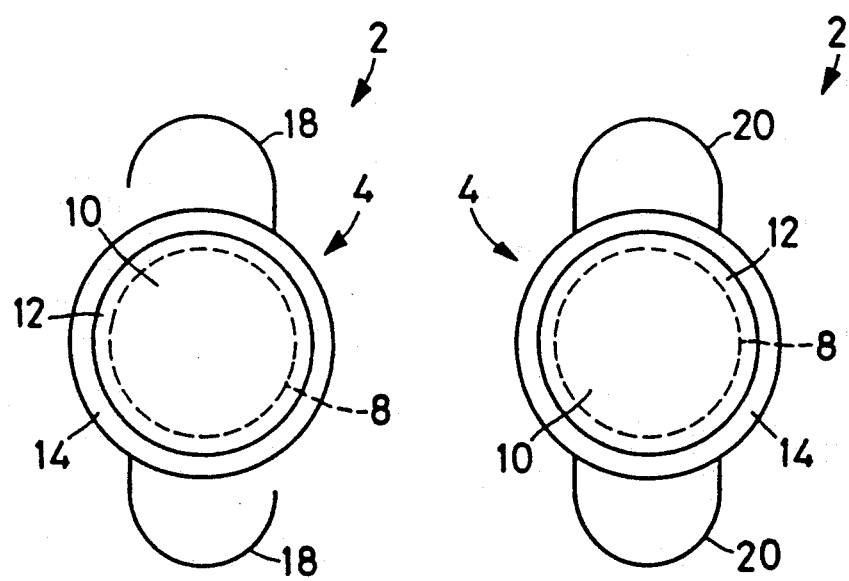
FIGS. 6a and 6b are plan views showing intraocular lens systems similar to that of FIG. 1, each lens system having a pair of loops secured to a posterior lens portion of a lens body.

Referring to FIGS. 5a and 5b, there is shown an intraocular lens system 2 which includes the lens body 4 as shown in FIGS. 1a and 1b. The lens system 2 further includes support means in the form of a pair of J-shaped loops 18 (FIG. 5a) or a pair of U-shaped loops 20 (FIG. 5b), such that the two loops 18 (20) are fixedly attached to the anterior lens portion 12 of the lens body 4 in diametrically opposed disposition with each other, more precisely, at diametrically opposed points on the periphery of the anterior lens portion 12. These loops 18, 20 serve to prevent the intraocular lens 4 from slipping or falling into the capsular bag. Referring next to FIGS. 6a and 6b, the intraocular lens system 2 has the lens body 4 as shown in FIGS. 1a and 1b, and a pair of J-shaped loops 18 (FIG. 6a) or a pair of U-shaped loops 20 (FIG. 5b) which are fixedly attached to the posterior lens portion 14 in diametrically opposed disposition with each other, more precisely, at diametrically opposed points on the periphery of the posterior lens portion 14. These loops 18, 20 serve to prevent the intraocular lens 4 from moving away from the capsular bag toward the cornea.

It will be readily understood that the intraocular lens of the invention may be provided with holes and tab members (protrusions formed on the the periphery of the lens), as in the conventional intraocular lens. These holes and tab members facilitate handling or manipulation of the intraocular lens with the use of forceps, such as insertion or adjustment of the lens into the eye chamber, or correction of the fixed position of the lens within the eye.

While the intraocular lenses 4, 13, 15, 17 of the illustrated embodiments as shown in FIGS. 1a through 4 are constructed such that the anterior and posterior lens portions 12, 14 of each lens have different dimensions and configurations, the anterior lens portion 12 may have substantially the same dimensions and configuration as the posterior lens portion 14 as described below. In this case, at least one support member such as a loop is provided on the posterior lens portion 14 for preventing the lens from slipping off from the capsular bag toward the cornea.

Figure 7A:
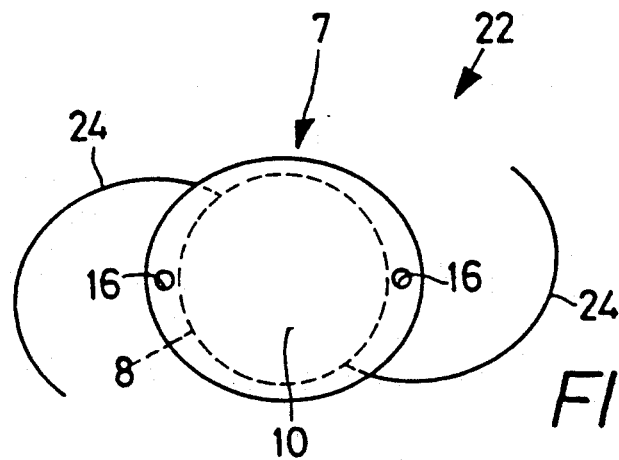
FIGS. 7a, 8a, 9a, 13a and 15a are plan views of further embodiments of the intraocular lens system of the present invention.
Figure 7B:
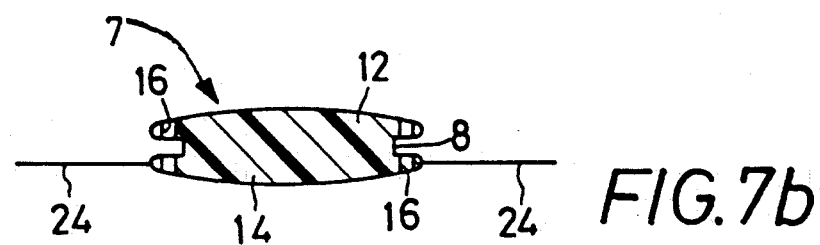
FIGS. 7b, 8b, 9b, 13b and 15b are vertical cross sectional views of the intraocular lens systems as shown in FIGS. 7a, 8a, 9a, 13a and 15a, respectively.

Referring to FIGS. 7a and 7b, there is shown an intraocular lens system 22 which consists of a lens body 7, and two support members 24, 24 that are fixedly secured to the posterior lens portion 14 of the lens body 7. Reference numerals 16 denote a pair of holes which serve to facilitate the handling of the lens with forceps, such as insertion of the lens into the eye, or correction of the fixed position of the lens within the eye.

More specifically, the anterior and posterior lens portions 12, 14 of the lens body 7 are both formed in oval configuration as viewed in the direction of the optical axis of the lens body 7. As is apparent from the cross sectional view of FIG. 7b, the anterior and posterior lens portions 12, 14 have opposite convex outer surfaces, and mutually facing flat inner surfaces which define the width of the groove 8 in the direction of the optical axis.

The groove 8 formed in the peripheral portion of the lens body 7 extends over the entire circumference of the body 7, such that the optically effective portion 10 is located radially inside the annular groove 8. It is desirable that the depth of the groove 8 is set within a range of 0.1 mm to 2 mm, and the width of the groove 8 is set within a range of 0.05 mm to 0.5 mm. If the width of the groove 8 is smaller than 0.05 mm, the annular flap portion of the anterior wall of the capsular bag surrounding the opening cannot be received and retained in the groove 8, whereby the intraocular lens system 22 cannot be secured in position within the opening in the capsular bag. If the width of the groove 8 is larger than 2 mm, the annular flap portion of the bag surrounding the opening tends to be disengaged from the groove 8. The optically effective portion 10 of the lens body 7 is desirably formed in circular configuration with the diameter of 4 mm to 9 mm.

In the instant embodiment, the anterior and posterior lens portions 12, 14 have substantially the same dimensions and configuration as viewed in the direction of the optical axis of the lens body 7, i.e., as seen in FIG. 7a. Accordingly, the annular groove 8 may have a comparatively large diameter, being formed on the radially extreme peripheral portion of the lens body 7 which corresponds to the radially outermost portion of the lens. In this arrangement, the optically effective portion 10 located radially inside the groove 8 may be sufficiently sized, permitting the lens body 7 to exhibit excellent optical capability even if the lens system 22 is dislocated from the nominal position in the eye.

In the lens system 22 of the instant embodiment, the pair of holes 16, 16 are formed in the radially peripheral portion of the lens body 7 so as to extend through both the anterior and posterior lens portions 12, 14. In this arrangement, a suitable material may be readily injected through these holes 16 into the capsular bag, as needed, after the intraocular lens system 22 is secured in position within the opening in the capsular bag. However, only one hole 16 may suffice for facilitating the insertion of the lens, correction of the lens position, and so forth. It is also to be understood that the present lens system does not necessarily require any hole as described above.

The support members 24, 24 of the present intraocular lens system 22 take the form of a pair of C-shaped loops which are fixedly attached to the posterior lens portion 14 of the lens body 7 in diametrically opposed disposition, at diametrically opposed points on the periphery of that lens portion 14. These loops 24, 24 serve to prevent the intraocular lens system 22 from slipping off from the capsular bag toward the cornea owing to an externally applied shock or a pressure applied from the vitreous humour, assuring significantly improved safety and stabilization of the lens system 22 within the eye.

Figure 8A:
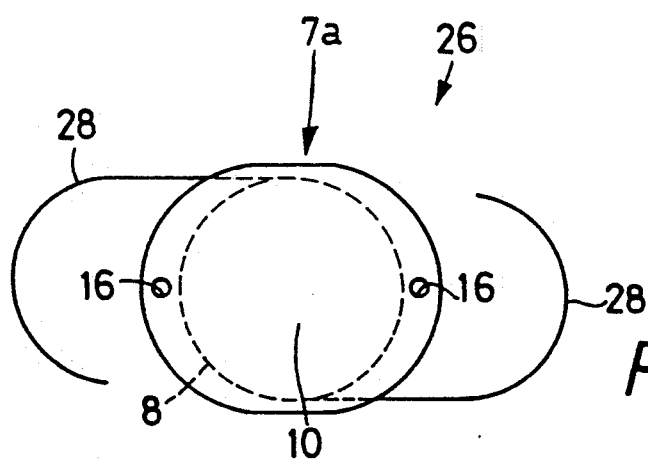
Figure 8B:
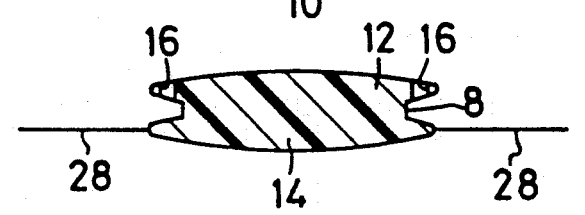

Referring next to FIGS. 8a, 8b, the anterior and posterior lens portions 12, 14 of the lens body 7a have a generally oval shape with diametrically opposite parallel straight edges, as viewed in the direction of the optical axis of the lens. As seen from the cross sectional view of FIG. 8b, the anterior and posterior lens portions 12, 14 have respective inner and outer convex surfaces. A pair of holes 16 are formed only through the anterior lens portion 12. The instant intraocular lens system 26 further includes a pair of J-shaped loops 28 which are fixedly secured to the posterior lens portion 14 in diametrically opposite disposition with each other, at diametrically opposite points on the periphery of the lens portion 14.

Figure 9A:
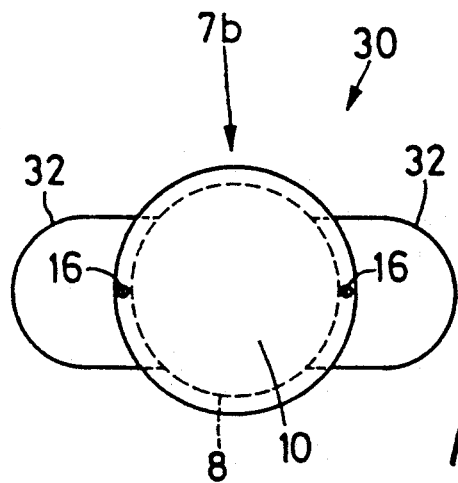
Figure 9B:
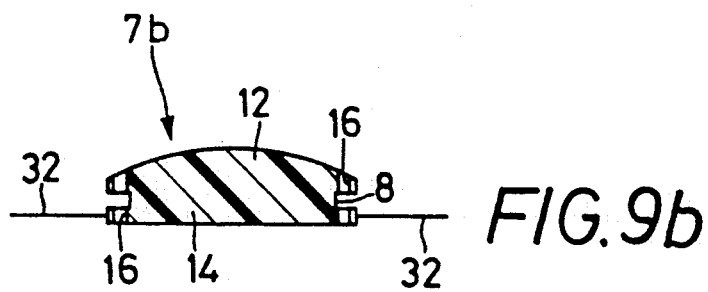

In the intraocular lens system 30 as illustrated in FIGS. 9a and 9b, the anterior and posterior lens portions 12, 14 of the lens body 7b have a circular shape diameter, as viewed in the direction of the optical axis of the lens. As seen from the cross sectional view of FIG. 9b, the anterior lens portion 12 has a convex outer surface and a flat inner surface, while the posterior lens portion 14 has opposite flat surfaces. The lens system 30 includes a pair of U-shaped loops 32, which are fixedly secured to the posterior lens portion 14 in diametrically opposite disposition, at diametrically opposite points on the periphery of the lens portion 14.

Figure 10:
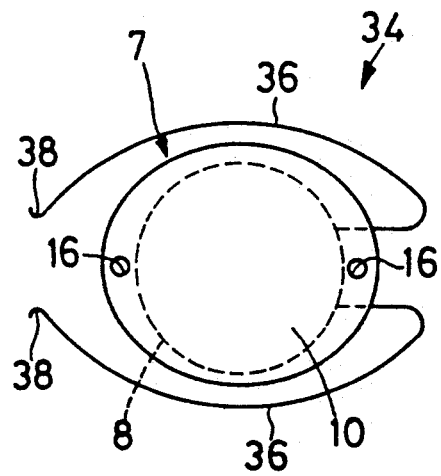
FIGS. 10, 11, 12 and 14 are plan views showing still further embodiments of the intraocular lens system of the present invention.
Figure 11:
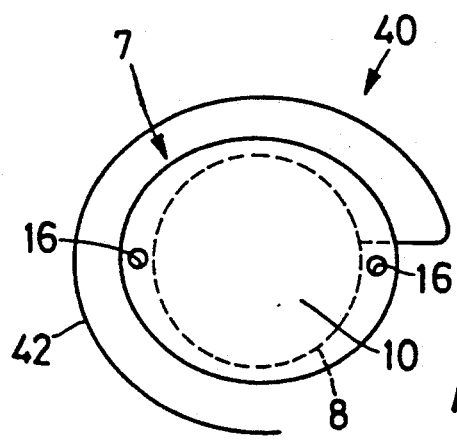
Figure 12:
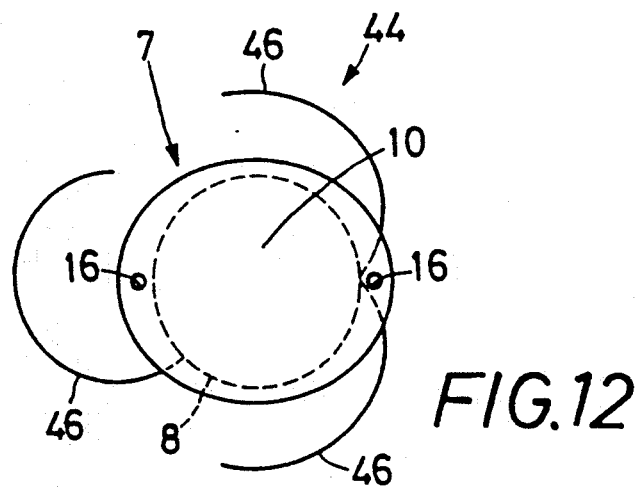
Figure 13A:
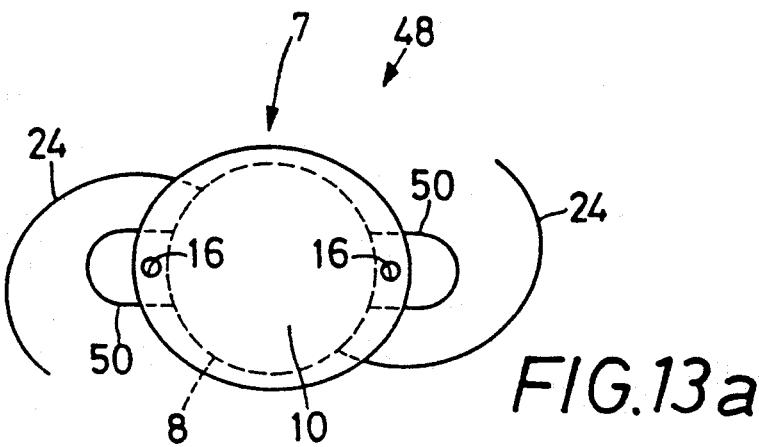
Figure 13B:
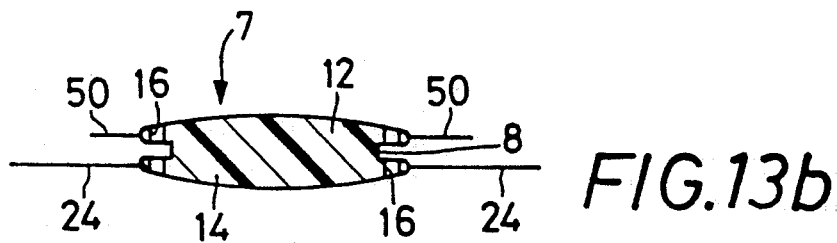

The intraocular lens systems 34, 40, 44, 48 as illustrated in FIGS. 10, 11, 12, 13a and 13b have respective lens bodies similar to the lens body 7 of the intraocular lens system 22 as shown in FIG. 7, and respective support means structurally different from that of the lens system 22. More specifically, the lens system 34 as shown in FIG. 10 has support means in the form of a pair of arched or bowlike loops 36, 36, which are secured to one of the longitudinally opposite end portions of the oval posterior lens portion 14, at two spaced-apart points on the periphery of the lens portion 14. These arched loops 36, 36 have respective engaging portions 38, 38 (so-called eyelets) formed at their free ends, which serve to facilitate the insertion of the lens into the eye by means of forceps. The intraocular lens system 40 as shown in FIG. 11 has a single arched loop 42 which is secured to one of the longitudinally opposite ends of the oval posterior lens portion 14, such that the loop 42 extends around the lens body 7, more precisely, over three quarters of the circumference of the body 7. The intraocular lens system 44 as shown in FIG. 12 has three C-shaped loops 46 which are fixedly attached to the posterior lens portion 14 at respective three points on the periphery of that portion 14. The intraocular lens system 48 as shown in FIGS. 13a and 13b has auxiliary support means in the form of a pair of U-shaped loops 50, 50 which are secured to the anterior lens portion 12, as well as the pair of C-shaped loops 24, 24 secured to the posterior lens portion 14. These U-shaped loops 50, 50 are fixedly attached to the anterior lens portion 12 in diametrically opposite points on the periphery of that portion 12. The C-shaped loops 24 and U-shaped loops 50 cooperate to prevent the intraocular lens system 48 from slipping off in the directions toward and away from the cornea after the lens system 50 is secured in position within the opening of the capsular bag.

Figure 14:
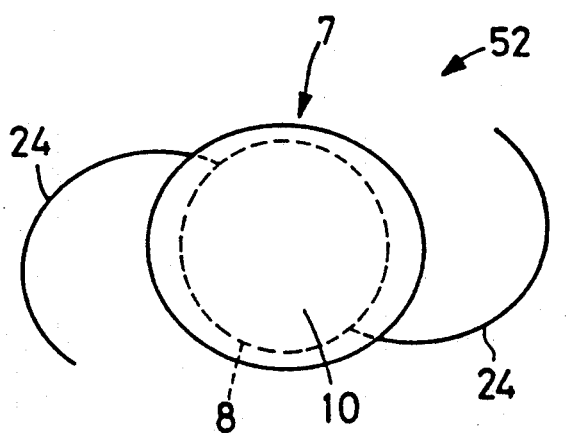
Figure 15A:
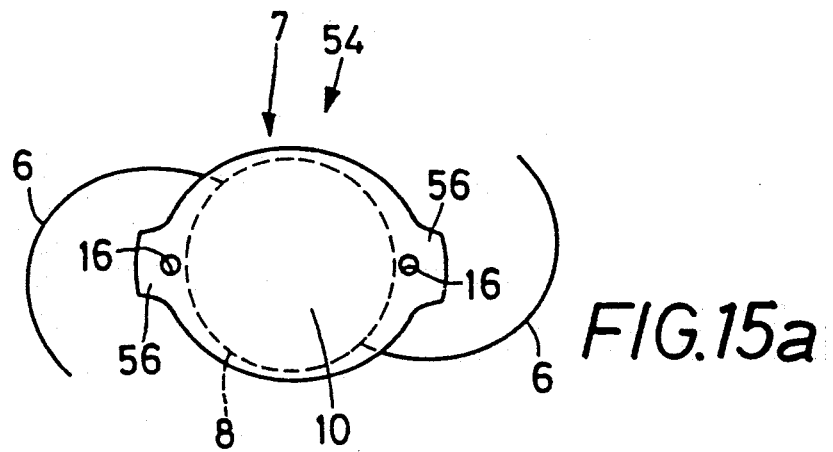
Figure 15B:
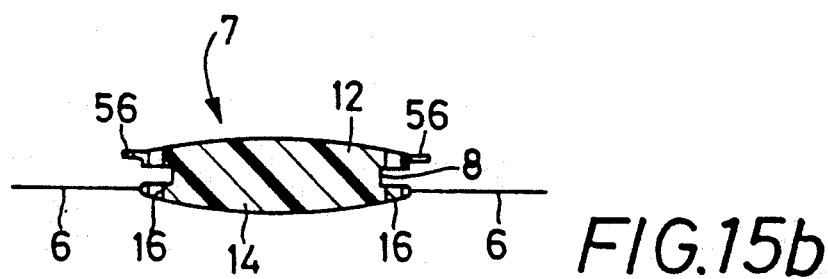

The intraocular lens system 52 as shown in FIG. 14 has the same structure as the above-described lens system 22 as shown in FIG. 7, except that the lens system 52 does not have holes (16) as provided in the lens system 22. In the intraocular lens system 54 as shown in FIGS. 15a and 15b, the lens body 7 is formed integrally with a pair of solid tabs 56, 56 at diametrically opposite parts of the anterior lens portion 12 in which the holes 16, 16 are provided. These tabs 56 further facilitate the handling of the lens with forceps, for example, for placing the lens in position in the eye.

Figure 16A:
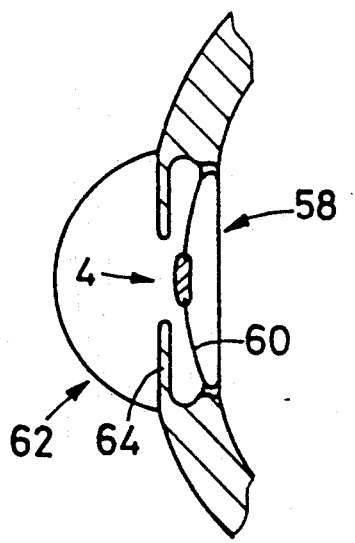
FIG. 16a is a cross sectional view indicating the position of the intraocular lens of FIG. 1 in the eyeball, when the lens is inserted into the eye.
Figure 16B:
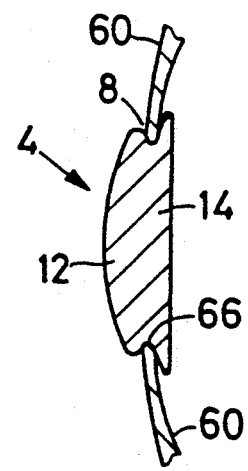
FIG. 16b is a view showing in enlargement the anterior wall of the capsular bag when the intraocular lens of FIG. 1 is mounted on the capsular bag.

The intraocular lens or lens system constructed as described above is inserted into the eye so that the lens is mounted on the capsular bag as illustrated in FIGS. 16a and 16b, by way of example. More specifically described referring to FIG. 16a which schematically shows the front portion of the eyeball in cross section, the intraocular lens 4 as shown in FIGS. 1a, 1b is mounted on the anterior wall 60 of the capsular bag 58 which normally accommodates the crystalline lens, after the removal of the nucleus of the crystalline lens from the bag. As shown in enlargement in FIG. 16b, the annular flap portion of the anterior wall 60 surrounding the circular opening 66 is received and retained within the annular groove 8 formed in the radially peripheral portion of the intraocular lens 4. In FIG. 16a, reference numerals 62 and 64 respectively denote the cornea and the iris of the eye.

There will be hereinafter described the procedure of mounting the intraocular lens 4 in position in the eye. Initially, a part of the posterior lens portion 14 (and the loop(s) if secured to the lens portion 14) is inserted through the circular opening 66 provided in the anterior wall 60 of the capsular bag 58, with the annular flap portion of the anterior wall 60 engaging the groove 8 in the lens 4. Prior to the insertion of the lens 4, the opening 66 is formed by the CCC (continuous circular capsulorhexis) method, so that the nucleus (protain material) of the crystalline lens is removed or extracted from the capsular bag 58 through the opening 66. This circular opening 66 has substantially the same diameter as the above-indicated optically effective portion 10 of the lens 4, whose periphery defines the bottom of the groove 8. Subsequently, the annular flap portion of the anterior wall 60 of the capsular bag 58 is inserted into the annular groove 8 in the lens 4, one part after another in the circumferential direction, by means of forceps, for example. Consequently, the annular flap portion of the bag 58 is received and retained within the groove 8 over the entire circumference thereof. In this respect, it is to be noted that the anterior wall 60 of the capsular bag 58 is expansible enough to permit the insertion of the posterior lens portion 14 of the lens 4 into the capsular bag 58 through the opening 66. With the entire circumference of the annular flap portion being received within the groove 8, the intraocular lens 4 is fixedly mounted on the anterior wall 60 of the capsular bag 58, as shown in FIGS. 16a, 16b.

While the natural crystalline lens of the eye assumes a generally flat shape after the nucleus of the lens is surgically removed, the intraocular lens may be inserted into position in the eye in this condition without causing any problems to the functions of the eye. However, it is possible to inject a suitable material into the capsular bag, so that the injected material gives the intraocular lens elasticity similar to that of the original natural crystalline lens, and makes it possible to adjust the eyesight of the intraocular lens.

The material to be injected into the capsular bag may be suitably selected from natural substances such as pullulan, sodium alginate, agar-agar, hyaluronic acid, chitosan, collagen, elastin, and methyl cellulose, or from synthetic substances such as polyvinyl alcohol, polyacrylamide, polyacrylic acid, silicone gel, polyvinyl pyrrolidone and gelatin. To avoid leakage of the thus injected material through the opening formed through the capsular bag, the selected material may be first injected into a balloon member as disclosed in laid-open Publications Nos. 63-200755 and 64-32859 of unexamined Japanese Patent Applications, so that the balloon member filled with the selected material is then inserted into the capsular bag. Especially where the selected material is not suited for biological or optical use, the balloon member as described above may be preferably used for assuring improved safety.

Alternatively, the injection of the selected material into the capsular bag 58 may be accomplished by spreading the annular flap portion of the capsular bag 58 apart from the bottom of the groove 8 in the lens body 4 while the lens 4 is held in place on the capsular bag 58, to thereby form a clearance between the flap portion and the groove 8, through which the selected material is injected into the capsular bag 58 by a suitable injector. When the lens body 7 has a hole or holes 16 formed through the posterior lens portion 14, as in the embodiment of FIG. 7, for example, an injector may be inserted through the hole 16 so as to inject the selected material into the capsular bag 58, without causing excessive expansion of the annular flap portion to permit the injection of the material. In this case, too, the selected material may be injected into the capsular bag without suffering from leakage of the material, since the opening 66 in the anterior wall 60 of the bag 58 is closed by the lens body 7 held in place on the capsular bag 58. When the injector is pulled out of the hole 16 upon completion of the injection of the selected material, the annular flap portion of the bag 58 naturally moves to fill the groove 8 in the lens body 7, whereby the leakage of the injected material is substantially avoided.

What is claimed is:

1. An intraocular lens for implanting within a generally circular opening in an anterior wall of a capsular bag of an eye, comprising:

a lens body including an annular groove in a peripheral portion of said lens body, wherein said annular groove is in a plane substantially perpendicular to an optical axis of said lens body, said lens body comprising:

a) an optically effective portion located substantially radially inside said annular groove, and b) an anterior lens portion and a posterior lens portion on respective anterior and posterior sides of said annular groove, and wherein said annular groove is adapted to receive an annular flap portion which surrounds a generally circular opening in an anterior wall of a capsular bag of an eye; and support means for holding said lens body against at least one of opposite surfaces of such an anterior wall of such a capsular bag, thereby preventing displacement of said lens body, said support means comprising at least one loop which is secured to one of said anterior and posterior lens portions of said lens body so as to extend radially outwardly from the periphery of one of said anterior or posterior lens portions.

2. An intraocular lens of claim 1, wherein said annular groove has a depth within 0.1 to 2.0 mm.

3. An intraocular lens of claim 1, wherein said anterior and posterior lens portions both have an oval shape, as viewed in said axial direction.

4. An intraocular lens of claim 1 wherein said at least one loop comprises a pair of loops which are secured to said posterior lens portion at substantially diametrically opposite points on the periphery of the posterior lens portion.

5. An intraocular lens of claim 1 wherein said lens body has at least one hole formed in said peripheral portion so as to extend through at least one of said anterior and posterior portions in said axial direction.

6. An intraocular lens of claim 1 wherein said annular groove has a width within a range of 0.05 mm to 0.5 mm as measured in said axial direction.

7. An intraocular lens for implanting within a generally circular opening in an anterior wall of a capsular bag of an eye comprising:

a lens body including an annular groove in a peripheral portion of said lens body, wherein said annular groove is in a plane substantially perpendicular to an optical axis of said lens body and has a depth in a range of 0.1 mm to 2.0 mm, and wherein said lens body comprises:

a) an optically effective portion located substantially radially inside said annular groove, and b) an anterior lens portion and a posterior lens portion on respective anterior and posterior sides of said annular groove, and wherein said annular groove is adapted to receive an annular flap portion which surrounds a generally circular opening in an anterior wall of a capsular bag of an eye; and support means for holding said lens body against at least one of opposite surfaces of an anterior wall of a capsular bag, thereby preventing displacement of said lens body, said support means comprising at least a pair of loops, each of said pair of loops secured to said anterior or posterior lens portions of said lens body at substantially diametrically opposite points on a periphery of said anterior or posterior lens portions of said lens body.

8. An intraocular lens for implanting within a generally circular opening in an anterior wall of a capsular bag of an eye comprising:

a lens body including an annular groove in a peripheral portion of said lens body, wherein said annular groove is in a plane substantially perpendicular to an optical axis of said lens body, said lens body comprising:

a) an optically effective portion located substantially radially inside said annular groove, and b) an anterior lens portion and a posterior lens portion on respective anterior and posterior sides of said annular groove, said anterior and posterior lens portions having substantially the same dimensions and the same shape as viewed in an axial direction parallel to said optical axis of the lens body, and wherein said annular groove is adapted to receive an annular flap portion which surrounds a generally circular opening in an anterior wall of a capsular bag of an eye; and support means for holding said lens body against a posterior surface of such an anterior wall of such a capsular bag, said support means comprising at least one loop secured to said posterior lens portion so as to extend radially outwardly from the periphery of said posterior lens portion.

9. An intraocular lens of claim 8, wherein said support means further comprises at least one loop secured to said anterior lens portion so as to extend radially outwardly from the periphery of said anterior lens portion.

10. An intraocular lens of claim 8, wherein said annular groove has a depth within 0.1 to 2.0 mm.

11. An intraocular lens system of claim 1, wherein both of said anterior and posterior lens portions have a generally oval shape with diametrically opposite parallel straight edges as viewed in said axial direction.

12. An intraocular lens system of claim 1, wherein both of said anterior and posterior lens portions have a circular shape with the same diameter as viewed in said axial direction.

13. An intraocular lens system of claim 1, wherein said lens body is formed with at least one tab member which extends radially outwardly beyond the periphery of at least one of said anterior and posterior portions.

* * * * *

UNITED STATES PATENT AND TRADEMARK OFFICE
CERTIFICATE OF CORRECTION

PATENT NO. : 5,171,320
DATED : December 15, 1992
INVENTOR(S) : Okihiro Nishi, et al.

It is certified that error appears in the above-identified patent and that said Letters Patent is hereby corrected as shown below:

On the title page, under item [19], after "Nishi", insert —et al.—; and in item [75], change "Inventor: Okihiro Nishi, Katano, Japan" to —Inventors: Okihiro Nishi, Katano; Yuji Sakka, Kitakyushu; Yoshiharu Yamada, Toyota; Akihiko Iinuma, Gifu, all of Japan—.

Signed and Sealed this

Twelfth Day of October, 1993

*Attest:*

BRUCE LEHMAN

*Attesting Officer*     *Commissioner of Patents and Trademarks*